US006297412B1

(12) United States Patent
Yokoyama et al.

(10) Patent No.: US 6,297,412 B1
(45) Date of Patent: Oct. 2, 2001

(54) PROCESS FOR PURIFYING DIFLUOROMETHANE

(75) Inventors: Takaaki Yokoyama; Koichi Yanase; Yasuhiro Suzuki, all of Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/788,591

(22) Filed: Feb. 21, 2001

(30) Foreign Application Priority Data

Feb. 22, 2000 (JP) .................................................. 12-044967

(51) Int. Cl.[7] .................................................. C07C 19/00
(52) U.S. Cl. .............................................................. 570/180
(58) Field of Search ............................................... 570/180

(56) References Cited

U.S. PATENT DOCUMENTS 2,640,086   5/1953   Baldwin .

FOREIGN PATENT DOCUMENTS 0 924 178   6/1999   (EP) .

*Primary Examiner*—Alan Siegel
(74) *Attorney, Agent, or Firm*—Oblon, Spivak, McClelland, Maier & Neustadt, P.C.

(57) ABSTRACT

A process for purifying difluoromethane, which comprises subjecting a mixture comprising difluoromethane and hydrogen fluoride to extraction treatment with at least one extractant selected from the following (a) and (b) to separate it by liquid separation into an extractant layer comprising the difluoromethane and the extractant as the main components, and a hydrogen fluoride layer comprising the hydrogen fluoride as the main component, and separating the difluoromethane from the extractant layer:

(a) Dichloromethane
(b) Chlorofluoromethane.

11 Claims, No Drawings

PROCESS FOR PURIFYING DIFLUOROMETHANE

The present invention relates to a process for purifying difluoromethane useful as e.g. a refrigerant.

Production of difluoromethane is, in many cases, carried out by a reaction method of fluorinating dichloromethane in a gas phase or a liquid phase in the presence of various catalysts such as antimony fluoride. In such production of difluoromethane, hydrogen fluoride (hereinafter referred to also as HF) is used in excess relative to dichloromethane as the starting material. Accordingly, in the reaction product obtained by the above reaction, a large amount of unreacted HF remains in addition to difluoromethane as the desired product, and it is necessary to remove HF from the reaction product.

In such separation of HF from the above reaction product, it is economically necessary to recover a large amount of HF contained in the reaction product simultaneously and to return it to the reaction system for re-use. However, difluoromethane and HF are mutually dissolved, and not only they are hardly separable by phase separation, but also they form an azeotropic mixture, whereby it is difficult to obtain difluoromethane of high purity containing no HF by simple distillation.

Heretofore, as a method of separating such a mixture comprising difluoromethane and HF, a method of employing sulfuric acid as an extractant for HF, is known as disclosed in WO98/08789.

In the above-mentioned conventional method of employing sulfuric acid as an extractant, in order to recycle HF extracted with sulfuric acid, it is necessary to distill it to separate sulfuric acid and recover HF, whereby there will be a problem due to its strong corrosiveness.

The present inventors have conducted a study for a method of separating HF from a mixture comprising difluoromethane and HF, which does not have the above-mentioned problem, and as a result, have arrived at the present invention.

Namely, the present invention provides a process for purifying difluoromethane, which comprises subjecting a mixture comprising difluoromethane and hydrogen fluoride to extraction treatment with at least one extractant selected from the following (a) and (b) to separate it by liquid separation into an extractant layer comprising the difluoromethane and the extractant as the main components, and a hydrogen fluoride layer comprising the hydrogen fluoride as the main component, and separating the difluoromethane from the extractant layer:

(a) Dichloromethane (b) Chlorofluoromethane.

The substances of the above (a) and (b) as extractants to be used in the present invention, correspond to a starting material for producing difluoromethane by fluorinating dichloromethane with HF and an intermediate compound obtained at the time of the production, respectively. They have structures similar to difluoromethane as the desired product. Accordingly, their physical properties were expected to be similar to those of difluoromethane. However, contrary to such expectation, the present inventors have found that they show a small mutual solubility to HF, while they show a large mutual solubility to difluoromethane.

Thus, according to the present invention, at least one substance selected from the above (a) and (b), is used as an extractant, whereby high purity difluoromethane and HF can be efficiently extracted and separated from a mixture comprising difluoromethane and HF, and it has further been found that the separated HF can be re-used by returning it to the reaction system for producing difluoromethane, without separating the extractant contained therein. This is possible since the extractants to be used in the present invention, are the starting material and the intermediate for difluoromethane, and the extractants dissolved in HF can be converted to difluoromethane as the desired product, by returning them to the reaction system.

Now, the present invention will be described in detail with reference to the preferred embodiments.

The mixture comprising difluoromethane and HF to be treated in the present invention, is the one comprising difluoromethane and HF as the main components, wherein the respective components are present in the form of liquid and/or gas. The proportions of difluoromethane and HF contained in the mixture are not particularly limited, but typically, the mixture contains from 5 to 1,000 parts by weight, preferably from 10 to 100 parts by weight, of HF, per 100 parts by weight of difluoromethane. If the amount of HF is smaller than 5 parts by weight, the effect of using the extractant tends to be small. On the other hand, if the amount of HF exceeds 1,000 parts by weight, the amount of difluoromethane dissolved in the HF layer tends to be large, whereby the separation efficiency tends to be poor.

A typical example of the mixture comprising difluoromethane and HF to be treated by the present invention, is a reaction product obtained by fluorinating dichloromethane with HF in the presence of various catalysts such as antimony fluoride. This reaction product contains, in addition to difluoromethane and HF, small amounts of the substances of (a) and (b) to be used as extractants in the present invention and e.g. hydrogen chloride, but the presence of such additional components will not adversely affect the operation of the present invention. It is rather advantageous that the substances of (a) and (b) are contained, since the amount of the extractant to be used, may be reduced.

The extractant to be used in the present invention is at least one member selected from (a) dichloromethane and (b) chlorofluoromethane. Such an extractant can be obtained as an intermediate during the production of difluoromethane, but may of course be supplied from exterior of the system. As the extractant of the present invention, it is particularly preferred to use dichloromethane (a) among (a) and (b), for the reason that the solubility of HF is low. Of course, the substances of (a) and (b) may be used in combination, and other extractants may be used in combination.

In the present invention, the amount of the extractant is preferably from 0.3 to 30 times by a molar ratio to the difluoromethane. If the amount of the extractant is smaller than 0.3 time, the extraction efficiency tends to be poor, and the difluoromethane tends to remain in the HF layer. On the other hand, if it exceeds 30 times, the efficiency for recovery of difluoromethane by distillation tends to be poor. Particularly preferably, the amount of the extractant is from 1 to 10 times.

In the present invention, the extraction treatment with the extractant can be carried out by adopting a method of contacting the extractant with the mixture comprising difluoromethane and HF as intimately as possible. Such a contacting method is not particularly limited. For example, stirring or contacting by means of a line mixer can be employed. The liquid separation is carried out by a known method. The extraction and the liquid separation may be conducted at the same time by using the same apparatus, or may be conducted separately by means of separate apparatus.

The temperature for the extraction and the liquid separation is preferably from −40 to 50° C., which is the temperature at which the extractant containing HF and difluoromethane after the extraction, will be liquefied. If the temperature is lower than −40° C., the cost for the cooling installation tends to be high, such being undesirable. On the other hand, if it exceeds 50° C., the treating pressure is required to be maintained to be high, whereby the cost for the apparatus tends to be high, such being undesirable. Particularly preferably, the extraction and the liquid separation are carried out at a temperature of from −30 to 30° C. The pressure is related to the temperature, but it is preferably from 0.1 to 3 MPa, particularly preferably from 0.1 to 1 MPa.

The above extraction treatment is followed by liquid separation into two layers i.e. an extractant layer comprising the difluoromethane and the extractant as the main components, and a HF layer comprising HF as the main component.

The extractant layer is preferably subjected to a common suitable post treatment such as alkali washing or distillation to remove HF which is contained in a small amount thereby to obtain a mixture consisting essentially of difluoromethane and the extractant. This mixture is subjected to a suitable separation treatment, preferably distillation, to obtain the difluoromethane which contains substantially no extractant. Otherwise, the extractant layer may be subjected directly to distillation treatment without preliminarily separating HF, and in some cases, a plurality of distillation treatments may be combined and the operation conditions are selected, to obtain the difluoromethane which contains substantially no HF or extractant.

On the other hand, the HF layer contains, in addition to HF, small amounts of difluoromethane and the extractant. However, the HF layer may be used separately as a starting material for HF, or, as mentioned above, may be recycled to the reaction step of fluorinating dichloromethane with HF, which is a step for producing difluoromethane. In the latter case, each component contained in the HF layer will be effectively utilized without creating any trouble, which is advantageous. The materials for various installations to be used for carrying out the process for the present invention, such as the extracting apparatus, the liquid separation apparatus, various distillation apparatus and pipings, may be of various types having corrosion resistance. Among them, it is preferred to use hastelloy, stainless steel, Monel, nickel or a material lined with a fluorine type resin.

Now, the present invention will be described in further detail with reference to Examples. However, it should be understood that the present invention is by no means restricted by these Examples.

EXAMPLE 1

Into a 500 ml autoclave (reactor) made of aluminum alloy and equipped with a stirrer and a reflux condenser, 100 g of $SbF_5$ (antimony fluoride catalyst) and 250 g of HF were charged, and after raising the temperature to 100° C. with stirring, 5 g/hr (0.25 mol/hr) of HF and 8.5 g/hr (0.1 mol/hr) of dichloromethane were continuously supplied into the reactor.

The reaction was carried out by withdrawing the formed gas continuously through the reflux condenser cooled to 0° C., so that the inner pressure of the reactor became 1.0 MPa (gauge pressure), whereby the crude gas was recovered in a metal container cooled to −60° C. The reaction was carried out for 40 hours, whereby 235 g of the crude liquid was recovered.

The above crude liquid was analyzed, whereby it was confirmed to have the composition as identified in Table 1.

TABLE 1

| Compounds | Proportions (mol %) |
| --- | --- |
| Difluoromethane | 74 |
| Chlorofluoromethane | 4 |
| Dichloromethane | 1 |
| HF | 21 |

This crude liquid was charged into an autoclave and maintained at 20° C., whereby the respective liquids remained as mutually dissolved. The crude liquid was further cooled to −30° C., but they remained as mutually dissolved. Whereas, when 980 g of dichloromethane was added as an extractant, and the mixture was stirred for one minute while maintaining the temperature at −30° C. and the pressure at 0.2 MPa and then left to stand still, the mixture separated into two layers in about 15 seconds to show a clear interface.

After being left to stand still for at least two minutes, the extractant layer and the hydrogen fluoride layer were separated. After measuring the weight, the extractant layer was washed with water and analyzed by gas chromatograph whereupon the amounts of the extractant and the difluoromethane were obtained using the calibration curve preliminarily prepared. Further, the amount of hydrogen fluoride contained in the washed aqueous layer was obtained by titration with sodium hydroxide. On the other hand, the hydrogen fluoride layer was subjected to weight measurement, and then its composition was analyzed in the same manner as for the extractant layer. The results are shown in Table 2.

TABLE 2

| Extractant layer | | Hydrogen fluoride layer | |
| --- | --- | --- | --- |
| Compounds | Weight | Compounds | Weight |
| Hydrogen fluoride | 1 g | Hydrogen fluoride | 21 g |
| Difluoromethane | 176 g | Difluoromethane | 20 g |
| Chlorofluoromethane | 12 g | Chlorofluoromethane | 1 g |
| Dichloromethane | 972 g | Dichloromethane | 11 g |

As the obtained extractant layer, 90% of difluoromethane was recovered, and as the hydrogen fluoride layer, 95% of hydrogen fluoride was recovered. The above extractant layer was subjected to distillation to separate dichloromethane as the extractant by a pressure distillation apparatus and then subjected in a gas state to bubbling into 100 g of a 10 wt % potassium hydroxide aqueous solution at room temperature to remove remaining hydrogen fluoride, followed by separation of impurities by a pressure distillation apparatus to obtain difluoromethane having a purity of at least 99%. Dichloromethane separated by distillation was useful again as an extractant.

On the other hand, the obtained HF layer was recycled as it was to a reaction apparatus for continuous fluorination of dichloromethane employing the antimony fluoride catalyst, whereby no change was observed in the result of the fluorination reaction.

EXAMPLE 2

200 g of difluoromethane and 20 g of hydrogen fluoride were charged into an autoclave, and cooled to −30° C. Then, 1000 g of chlorofluoromethane was added as an extractant thereto. After stirring for 1 minute while maintaining the temperature at −30° C. and the pressure at 0.2 MPa, the mixture was left to stand still, whereby it was separated into two layers in about 15 seconds to show a clear interface.

After being left to stand still for further at least two minutes, the extractant layer and the hydrogen fluoride layer were separated. After measuring the weight, the extractant layer was washed with water and then analyzed by gas chromatograph, whereupon the amounts of the extractant and the difluoromethane were obtained using a calibration curve preliminarily prepared. Further, the amount of hydrogen fluoride contained in the washed aqueous layer was obtained by titration with sodium hydroxide.

On the other hand, the hydrogen fluoride layer was subjected to the weight measurement, and then its composition was analyzed in the same manner as for the extractant layer. The results are shown in Table 3.

TABLE 3

| Extractant layer | | Hydrogen fluoride layer | |
| --- | --- | --- | --- |
| Compounds | Weight | Compounds | Weight |
| Hydrogen fluoride | 1 g | Hydrogen fluoride | 19 g |
| Difluoromethane | 180 g | Difluoromethane | 20 g |
| Chlorofluoromethane | 978 g | Chlorofluoromethane | 22 g |

As the extractant layer, 90% of difluoromethane was recovered, and as the hydrogen fluoride layer, 95% of hydrogen fluoride was recovered.

The extractant layer was distilled to separate chlorofluoromethane as the extractant by a pressure distillation apparatus and then subjected in a gas state to bubbling in 100 g of a 10 wt % potassium hydroxide aqueous solution at room temperature to remove remaining HF, followed by distillation by a pressure distillation apparatus, to obtain difluoromethane having a purity of at least 99%.

According to the process of the present invention, a specific extractant is employed, whereby it is possible to effectively and easily separate difluoromethane and HF which are usually hardly separable, and it is possible to recover difluoromethane in high purity and in good yield. HF and the extractant used may be returned to the step of producing difluoromethane without purification, and they can be recycled for used as starting materials, without being accumulated, which is industrially very advantageous.

The entire disclosure of Japanese Patent Application No. 2000-044967 filed on Feb. 22, 2000 including specification, claims, drawings and summary are incorporated herein by reference in its entirety.

What is claimed is:

1. A process for purifying difluoromethane, which comprises subjecting a mixture comprising difluoromethane and hydrogen fluoride to extraction treatment with at least one extractant selected from the following (a) and (b) to separate it by liquid separation into an extractant layer comprising the difluoromethane and the extractant as the main components, and a hydrogen fluoride layer comprising the hydrogen fluoride as the main component, and separating the difluoromethane from the extractant layer:

(a) Dichloromethane (b) Chlorofluoromethane.

2. The process according to claim 1, wherein the proportion of HF contained in the mixture is from 5 to 1000 parts by weight, per 100 parts by weight of the difluoromethane.

3. The process according to claim 1, wherein the proportion of HF contained in the mixture is from 10 to 100 parts by weight, per 100 parts by weight of the difluoromethane.

4. The process according to claim 1, wherein the amount of the extractant is from 0.3 to 30 times (by a molar ratio) to the difluoromethane contained in the mixture.

5. The process according to claim 1, wherein the amount of the extractant is from 1 to 10 times (by a molar ratio) to the difluoromethane contained in the mixture.

6. The process according to claim 1, wherein the liquid separation to obtain the extractant layer and the hydrogen fluoride layer, is carried out at a temperature of from −40° C. to 50° C. under a pressure of from 0.1 to 3 MPa.

7. The process according to claim 6, wherein the temperature is from −30° C. to 30° C.

8. The process according to claim 6, wherein the pressure is from 0.1 to 1 MPa.

9. The process according to claim 1, wherein the extractant layer is distilled to separate the difluoromethane from the extractant layer, and the extractant is returned to the step of extraction treatment.

10. The process according to claim 1, wherein the mixture is a reaction product obtained from a reaction which comprises fluorinating dichloromethane with hydrogen fluoride.

11. The process according to claim 10, wherein the hydrogen fluoride layer is returned to the reaction step to obtain the mixture, without removing the extractant and the difluoromethane contained therein.

* * * * *